(12) United States Patent
Yamaguchi et al.

(10) Patent No.: US 7,036,933 B2
(45) Date of Patent: May 2, 2006

(54) MODEL EYE FOR EYE CHARACTERISTIC MEASURING DEVICE AND CALIBRATION METHOD FOR THE SAME

(75) Inventors: Tatsuo Yamaguchi, Tokyo (JP); Naoki Nakazawa, Tokyo (JP); Toshifumi Mihashi, Tokyo (JP); Yoko Hirohara, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 485 days.

(21) Appl. No.: 10/365,618

(22) Filed: Feb. 13, 2003

(65) Prior Publication Data

US 2003/0174280 A1 Sep. 18, 2003

(30) Foreign Application Priority Data

Feb. 15, 2002 (JP) ............................. 2002-037684

(51) Int. Cl.
*A61B 3/10* (2006.01)
(52) U.S. Cl. ........................................ 351/205; 351/212
(58) Field of Classification Search ................ 351/200, 351/205, 212, 221
See application file for complete search history.

(56) References Cited

U.S. PATENT DOCUMENTS

| 1,630,944 | A |   | 5/1927 | Ingersoll |         |
|-----------|---|---|--------|-----------|---------|
| 5,042,938 | A | * | 8/1991 | Shimozono | 351/205 |
| 5,141,302 | A | * | 8/1992 | Arai et al. | 351/205 |
| 5,532,770 | A |   | 7/1996 | Schneider et al. | |

(Continued)

FOREIGN PATENT DOCUMENTS

DE  43 13 031 A1  10/1994

OTHER PUBLICATIONS

Thibos et al., "Standards for Reporting the Optical Aberrations of Eyes," V. Lakshminarayanan (Ed.) Trends in Optics and Photonics, Optical Society of America, Washington, DC, pp. 232-244.*

(Continued)

*Primary Examiner*—Ali Imam
*Assistant Examiner*—John R. Sanders
(74) *Attorney, Agent, or Firm*—Foley & Lardner LLP (57) ABSTRACT

A model eye for an eye characteristic measuring device and a calibration method for the model eye. The model eye can have various aberrations and/or power characteristics to be formed by a combination of a refractive-type lens and a phase plate for adding aberration and can be used to confirm the accuracy of wavefront measurement or the like of the eye characteristic measuring device. The model eye includes an anterior eye lens forming a predetermined power to be given to the model eye, a diffusion surface diffusing and reflecting incident light, the diffusion surface being disposed at an image point position corresponding to the predetermined power in relationship to the anterior eye lens, and an aberration adding member giving a predetermined aberration to an area between the anterior eye lens and the diffusion surface. Power and aberration required for the model eye are formed by the anterior eye lens and the phase plate.

15 Claims, 9 Drawing Sheets

U.S. PATENT DOCUMENTS

| | | | |
|---|---|---|---|
| 5,875,017 A * | 2/1999 | Ohnuma et al. | 351/205 |
| 6,082,856 A | 7/2000 | Dunn et al. | |
| 6,485,142 B1 * | 11/2002 | Sheehy et al. | 351/203 |
| 6,626,535 B1 * | 9/2003 | Altmann | 351/177 |
| 6,637,884 B1 * | 10/2003 | Martino | 351/212 |
| 6,739,721 B1 * | 5/2004 | Altmann | 351/212 |
| 6,802,609 B1 * | 10/2004 | Mihashi et al. | 351/221 |
| 2002/0041359 A1 * | 4/2002 | Mihashi et al. | 351/221 |
| 2004/0246440 A1 * | 12/2004 | Andino et al. | 351/177 |

OTHER PUBLICATIONS

Kirschkamp, T., et al., "Construction of a Model Eye to Simulate Purkinje Reflections for the Determination of the Radii of Curvature and of the Position of the Crystalline Lens of the Eye," Biomedizinische Technik, vol. 66, No. 43, 1998, pp. 318-325.

* cited by examiner

EXAMPLE OF PHASE PLATE INSERTED
IN TILTED STATE TO PREVENT REFLECTION

Fig. 5

4
ND FILTER

2
DIFFUSION SURFACE HAVING
INCREASED REFLECTANCE $$\begin{bmatrix}
n & m & \\
0 & 0 & 1 \\
1 & 0 & r\sin(t) \\
1 & 1 & \cos(t)\,r \\
2 & 0 & r^2\sin(2t) \\
2 & 1 & 2r^2-1 \\
2 & 2 & r^2\cos(2t) \\
3 & 0 & r^3\sin(3t) \\
3 & 1 & (3r^3-2r)\sin(t) \\
3 & 2 & (3r^3-2r)\cos(t) \\
3 & 3 & r^3\cos(3t) \\
4 & 0 & r^4\sin(4t) \\
4 & 1 & (4r^4-3r^2)\sin(2t) \\
4 & 2 & 6r^4-6r^2+1 \\
4 & 3 & (4r^4-3r^2)\cos(2t) \\
4 & 4 & r^4\cos(4t) \\
5 & 0 & r^5\sin(5t) \\
5 & 1 & (5r^5-4r^3)\sin(3t) \\
5 & 2 & (10r^5-12r^3+3r)\sin(t) \\
5 & 3 & (10r^5-12r^3+3r)\cos(t) \\
5 & 4 & (5r^5-4r^3)\cos(3t) \\
5 & 5 & r^5\cos(5t) \\
6 & 0 & r^6\sin(6t) \\
6 & 1 & (6r^6-5r^4)\sin(4t) \\
6 & 2 & (15r^6-20r^4+6r^2)\sin(2t) \\
6 & 3 & 20r^6-30r^4+12r^2-1 \\
6 & 4 & (15r^6-20r^4+6r^2)\cos(2t) \\
6 & 5 & (6r^6-5r^4)\cos(4t) \\
6 & 6 & r^6\cos(6t)
\end{bmatrix}$$

Fig. 6

$$
\begin{matrix}
n & m & \\
0 & 0 & 1 \\
1 & 0 & y \\
1 & 1 & x \\
2 & 0 & 2yx \\
2 & 1 & 2x^2 + 2y^2 - 1 \\
2 & 2 & x^2 - y^2 \\
3 & 0 & 3yx^2 - y^3 \\
3 & 1 & 3yx^2 + 3y^3 - 2y \\
3 & 2 & 3x^3 + 3xy^2 - 2x \\
3 & 3 & x^3 - 3xy^2 \\
4 & 0 & 4yx^3 - 4y^3 x \\
4 & 1 & 8yx^3 + 8y^3 x - 6yx \\
4 & 2 & 6x^4 + 12x^2 y^2 + 6y^4 - 6x^2 - 6y^2 + 1 \\
4 & 3 & 4x^4 - 4y^4 - 3x^2 + 3y^2 \\
4 & 4 & x^4 - 6x^2 y^2 + y^4 \\
5 & 0 & 5yx^4 - 10y^3 x^2 + y^5 \\
5 & 1 & 15yx^4 + 10y^3 x^2 - 5y^5 - 12yx^2 + 4y^3 \\
5 & 2 & 10yx^4 + 20y^3 x^2 + 10y^5 - 12yx^2 - 12y^3 + 3y \\
5 & 3 & 10x^5 + 20x^3 y^2 + 10xy^4 - 12x^3 - 12xy^2 + 3x \\
5 & 4 & 5x^5 - 10x^3 y^2 - 15xy^4 - 4x^3 + 12xy^2 \\
5 & 5 & x^5 - 10x^3 y^2 + 5xy^4 \\
6 & 0 & 6yx^5 - 20y^3 x^3 + 6y^5 x \\
6 & 1 & 24yx^5 - 24y^5 x - 20yx^3 + 20y^3 x \\
6 & 2 & 30yx^5 + 60y^3 x^3 + 30y^5 x - 40yx^3 - 40y^3 x + 12yx \\
6 & 3 & 20x^6 + 60x^4 y^2 + 60x^2 y^4 + 20y^6 - 30x^4 - 60x^2 y^2 - 30y^4 + 12x^2 + 12y^2 - 1 \\
6 & 4 & 15x^6 + 15x^4 y^2 - 15x^2 y^4 - 15y^6 - 20x^4 + 20y^4 + 6x^2 - 6y^2 \\
6 & 5 & 6x^6 - 30x^4 y^2 - 30x^2 y^4 + 6y^6 - 5x^4 + 30x^2 y^2 - 5y^4 \\
6 & 6 & x^6 - 15x^4 y^2 + 15x^2 y^4 - y^6
\end{matrix}
$$

Fig. 7

Fig. 8 MODEL EYE ABERRATION MEASURING METHOD USING INTERFEROMETER

(A) PHASE PLATE NOT REPLACED

| (PHASE PLATE) POSITION · CHANGE | 1 | 2 | 3 |
|---|---|---|---|
| REFRACTIVE POWER | 0D | −1D | −2D |
| ABERRATION ($\mu$m) | 0.42 | 0.47 | 0.52 |
| MEASURED INTERFERENCE ($\mu$m) | 0.42 | 0.46 | 0.51 |

(B) PHASE PLATE NOT REPLACED

| (ANTERIOR EYE LENS) POSITION · CHANGE | 1 | 2 | 3 |
|---|---|---|---|
| REFRACTIVE POWER | 0D | −1D | −2D |
| ABERRATION ($\mu$m) | 0.42 | 0.38 | 0.32 |
| MEASURED INTERFERENCE ($\mu$m) | 0.42 | 0.38 | 0.31 |

(C) PHASE PLATE REPLACED

| (PHASE PLATE, ETC.) POSITION · CHANGE | 1 | 2 | 3 |
|---|---|---|---|
| REFRACTIVE POWER | 0D | −1D | −2D |
| ABERRATION ($\mu$m) | 0.42 | 0.42 | 0.43 |
| MEASURED INTERFERENCE ($\mu$m) | 0.42 | 0.41 | 0.42 |

Fig. 11

MODEL EYE FOR EYE CHARACTERISTIC MEASURING DEVICE AND CALIBRATION METHOD FOR THE SAME

BACKGROUND OF THE INVENTION

The present invention relates to a model eye for an eye characteristic measuring device and a calibration method for the model eye, and more particularly, to a model eye for an eye characteristic measuring device for confirming the measurement accuracy of a wave aberration measuring device for a subject eye as well as to a calibration method for the model eye.

In the related model eyes, their anterior eye lenses are made of spherical lenses and the retina are formed by its diffusion surfaces, and their optical characteristics only include refractive power, astigmatic power and spherical aberration. Accordingly, such related model eyes cannot be used for the calibration of eye characteristic measuring devices such as wavefront measurement devices.

SUMMARY OF THE INVENTION

It has recently been desired to provide a model eye capable of generating various wave aberrations and enabling calibration of an eye's optical characteristic measuring device.

Therefore, an object of the invention is to provide a model eye for an eye characteristic measuring device and a calibration method for the model eye. The model eye can have various aberrations and/or power characteristics to be formed by a combination of a refractive-type lens for use in the related model eye and a phase plate for adding aberration and can be used to confirm the accuracy of wavefront measurement or the like of the eye characteristic measuring device.

Another object of the invention is to provide a model eye for an eye characteristic measuring device and a calibration method for the model eye. The model eye is constructed so that a thin light beam is made incident on the model eye and the incident light beam is made to exit from the model eye as a reflected light beam which has a predetermined diameter larger than the diameter of the incident light beam and contains a predetermined higher order aberration.

According to one aspect of the invention, there is provided a model eye for an eye characteristic measuring device which includes:

an anterior eye lens forming a predetermined power to be given to the model eye;

a diffusion surface diffusing and reflecting incident light, the diffusion surface being disposed at an image point position corresponding to the predetermined power in relationship to the anterior eye lens; and a phase plate giving a predetermined aberration to an area between the anterior eye lens and the diffusion surface, wherein power and aberration required for the model eye are formed by the anterior eye lens and the phase plate.

According to another aspect of the invention, there is provided a calibration method for a model eye for an eye characteristic measuring device, the model eye comprising an anterior eye lens forming a predetermined power to be given to the model eye, a diffusion surface diffusing and reflecting incident light, the diffusion surface being disposed at an image point position corresponding to the predetermined power in relationship to the anterior eye lens, and a phase plate giving a predetermined aberration to an area between the anterior eye lens and the diffusion surface, and power and aberration required for the model eye being formed by the anterior eye lens and the phase plate, the calibration method including:

attaching a pinhole plate in place of the diffusion surface which is removably constructed;

performing alignment;

measuring optical characteristics such as optical aberrations of the model eye with an interferometer;

estimating the optical characteristics of the model eye from the measured result; and replacing the pinhole plate with the diffusion surface to calibrate the model eye.

BRIEF DESCRIPTION OF THE DRAWINGS

The invention will become more readily appreciated and understood from the following detailed description of preferred embodiments of the invention when taken in conjunction with the accompanying drawings, in which:

FIGS. 9(A) to 9(C) are explanatory views of design and manufacture examples of various model eyes;

DETAILED DESCRIPTION OF THE INVENTION

Preferred embodiments of the invention will be described below in detail with reference to the accompanying drawings.

1. Model Eye for Eye Characteristic Measuring Device

Figure 1:
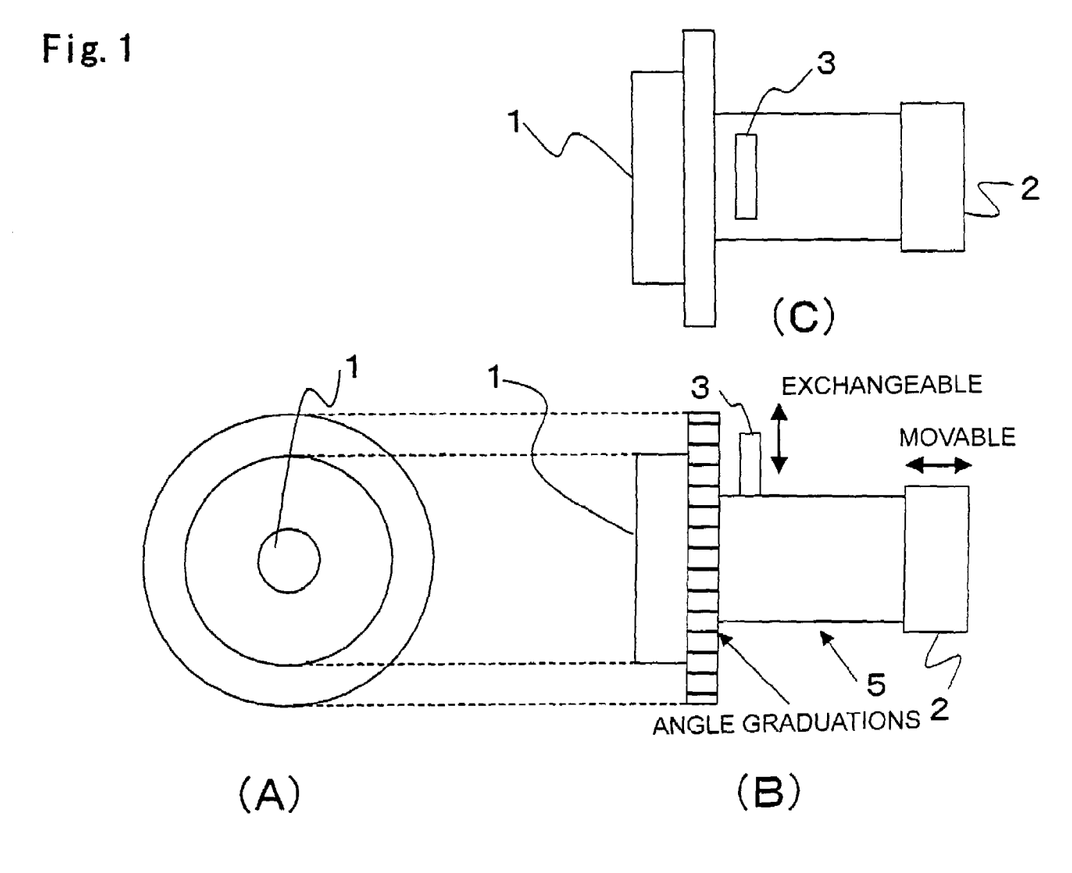
FIGS. 1A, 1B and 1C are views showing the construction of a first embodiment of the model eye for an eye characteristic measuring device according to the invention.
Figure 2:
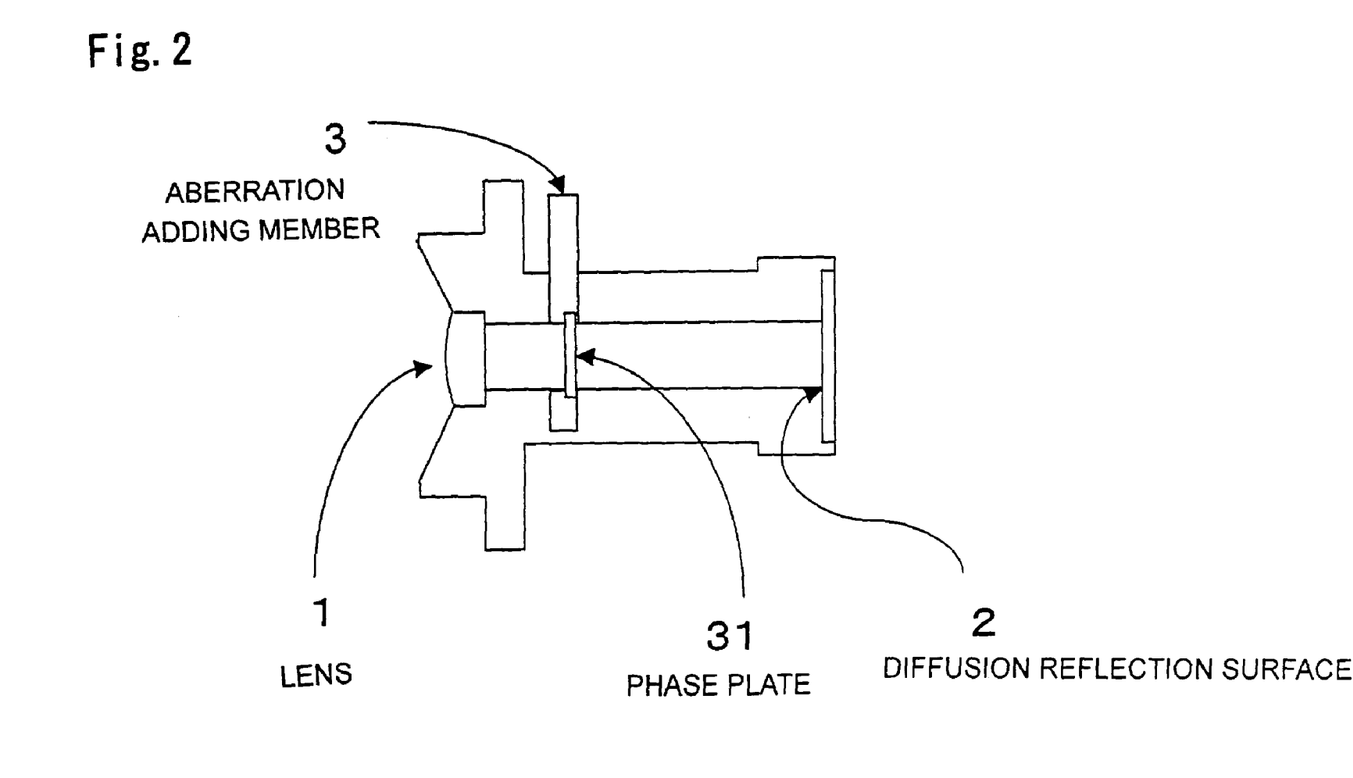
FIG. 2 is a cross-sectional view of the first embodiment of the model eye for an eye characteristic measuring device according to the invention.
Figure 3:
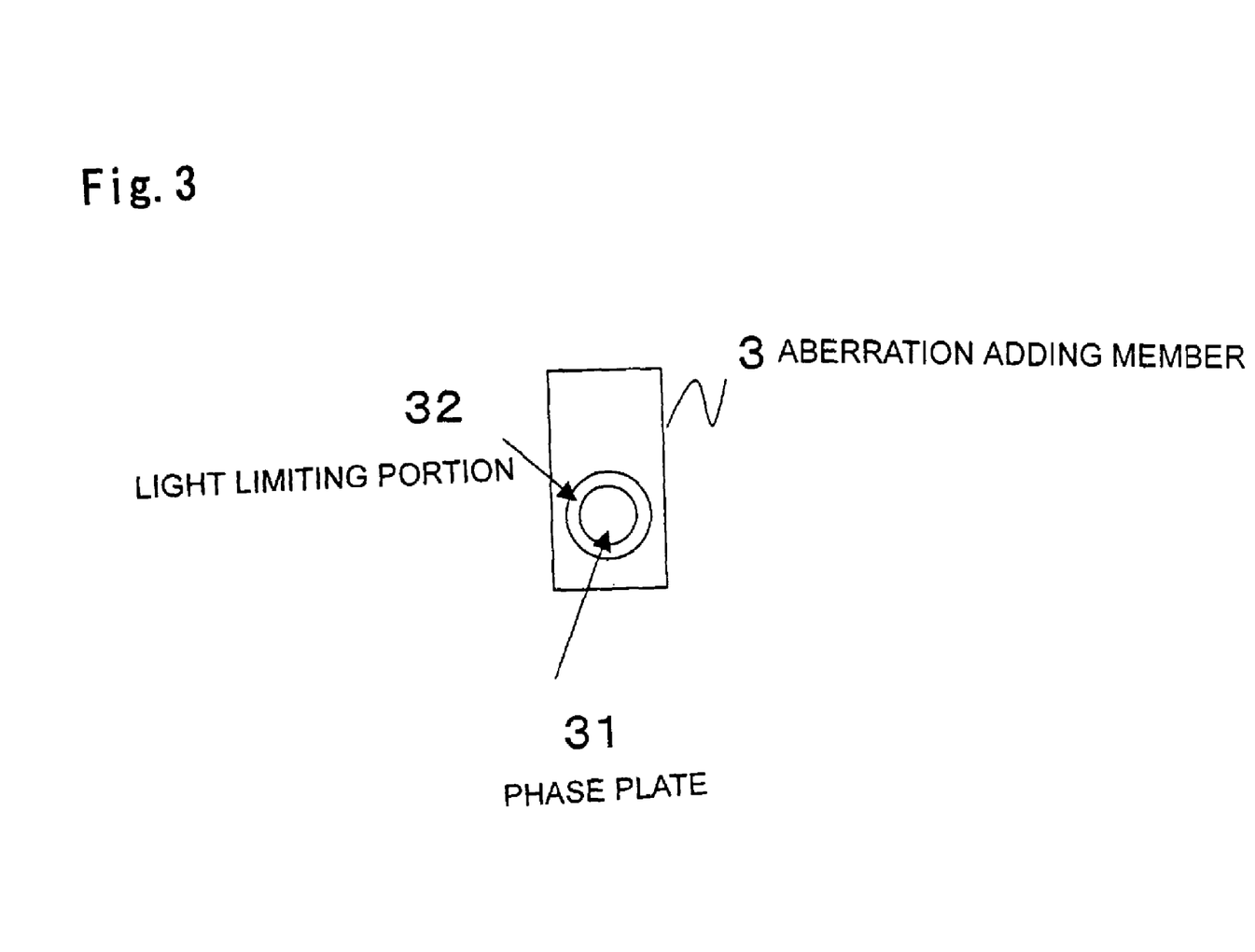
FIG. 3 is a view showing the construction of a phase plate.

FIGS. 1A, 1B and 1C are views showing the construction of a first embodiment of the model eye for an eye characteristic measuring device according to the invention. FIG. 1A is a front view, FIG. 1B is a side view, and FIG. 1C is a plane view. FIG. 2 is a cross-sectional view of the first embodiment of the model eye for the eye characteristic measuring device according to the invention. FIG. 3 is a view showing the construction of a phase plate.

The shown model eye includes an anterior eye lens 1, a diffusion surface 2, an aberration adding member 3 and a housing 5.

The anterior eye lens 1 forms a predetermined power to be given to the model eye. The front surface of the anterior eye lens 1 corresponds to the front surface of the cornea of an eye, and can be made to approximate a general radius of curvature of the front surface of the cornea (for example, 7.5 mm). In the case where the anterior eye lens 1 is formed of a lens having a residual aberration, the aberration adding member 3 can also be constructed to cancel this residual aberration and give a predetermined aberration. The anterior eye lens 1 is preferably formed of a lens having as small aberrations as possible, such as a combination of a plurality of lens elements and/or a cemented lens. Accordingly, even if conditions are modified, the anterior eye lens 1 can be designed so that variations in the influence of aberration due to the anterior eye lens 1 become as small as possible.

The diffusion surface 2 randomly diffuses and reflects incident light (for example, its reflectance may be made 10% or less, but is not limited to this numerical example). The diffusion surface 2 is disposed at an image point position (approximately at an image plane position) which corresponds to the predetermined power in relationship to the anterior eye lens 1 when the aberration adding member 3 is inserted. The diffusion surface 2 may also be disposed approximately at the focal length position of the anterior eye lens 1 that is determined when the aberration adding member 3 is inserted. The reflectance of the diffusion surface 2 may also be set to become sufficiently large with respect to the level of noise light such as reflected light from the aberration adding member 3.

The aberration adding member 3 gives the predetermined aberration to an area between the anterior eye lens 1 and the diffusion surface 2. The aberration adding member 3 adds the predetermined aberration by means of a phase plate 31 to an area which allows the amount of aberration to be detected in a diameter corresponding to a diameter to be measured on a pupil, and the influence of light coming from the outside of the diameter is eliminated by a light limiting portion 32 disposed around the phase plate 31. The phase plate 31 may use a binary optics element (BOE). It is appropriate that the position of the phase plate 31 coincide with the pupil position of the eye, but the position of the phase plate 31 may also be deviated to a small extent or disposed before the anterior eye lens 1 (refer to FIG. 11 which will be mentioned later).

The housing 5 covers a portion of the anterior eye lens 1, the phase plate 31 and the diffusion surface 2. Accordingly, the housing 5 is constructed to prevent foreign matter from adhering to the diffusion surface 2 and the phase plate 31. In addition, the housing 5 may also have graduations formed on the periphery of its metal part so that the angle of rotation of the model eye can be detected.

Figure 4:
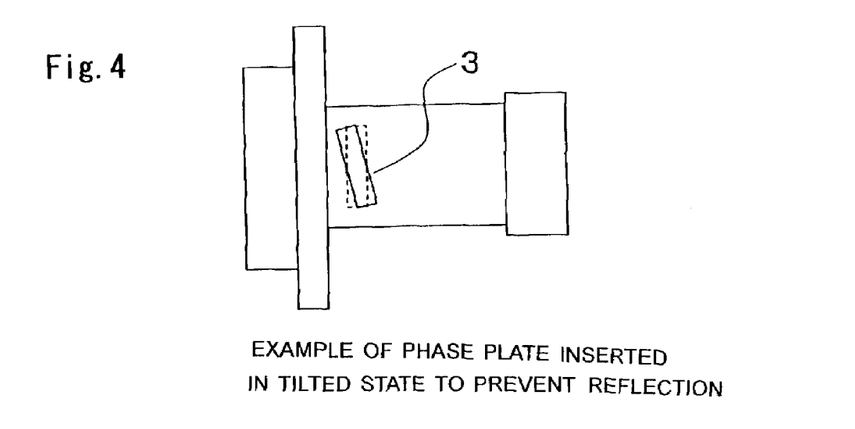
FIG. 4 is a view showing the construction of the second embodiment of the model eye for an eye characteristic measuring device according to the invention.

FIG. 4 is a view showing the construction of a second embodiment of the model eye for an eye characteristic measuring device. In the second embodiment, the aberration adding member 3 is disposed to be tilted at a predetermined (small) angle with respect to the optical axis as shown in FIG. 4 so that the influence of reflection from the aberration adding member 3 is restrained. In this construction, the phase plate 31 such as a binary optics element (BOE) is formed to take the tilt and the like into account.

Figure 5:
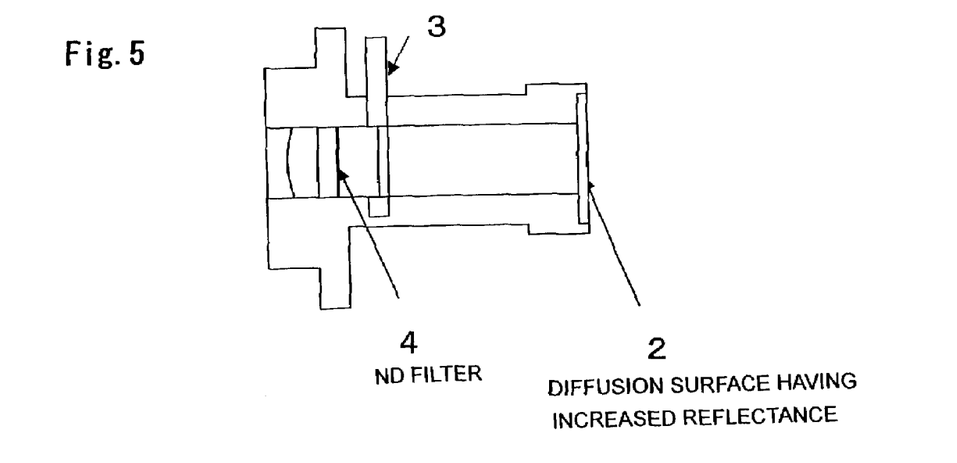
FIG. 5 is a view showing the construction of a third embodiment of the model eye for an eye characteristic measuring device according to the invention.

FIG. 5 is a view showing the construction of a third embodiment of the model eye for an eye characteristic measuring device. The third embodiment is intended for cases such as the case of increasing the reflectance of the diffusion surface 2 which corresponds to a fundus. In the case where the reflectance of the diffusion surface 2 is increased (for example, by several % to 30%, although the invention is not limited to this numerical example) to restrain the influence of reflection from the aberration adding member 3, a neutral density (ND) filter 4 or the like is disposed before the aberration adding member 3 so that the total amount of reflected light can be decreased to reduce the ratio of the amount of reflected noise light to the amount of light reflected from the fundus. The neutral density filter 4 may also be disposed before the anterior eye lens 1.

Figure 11:
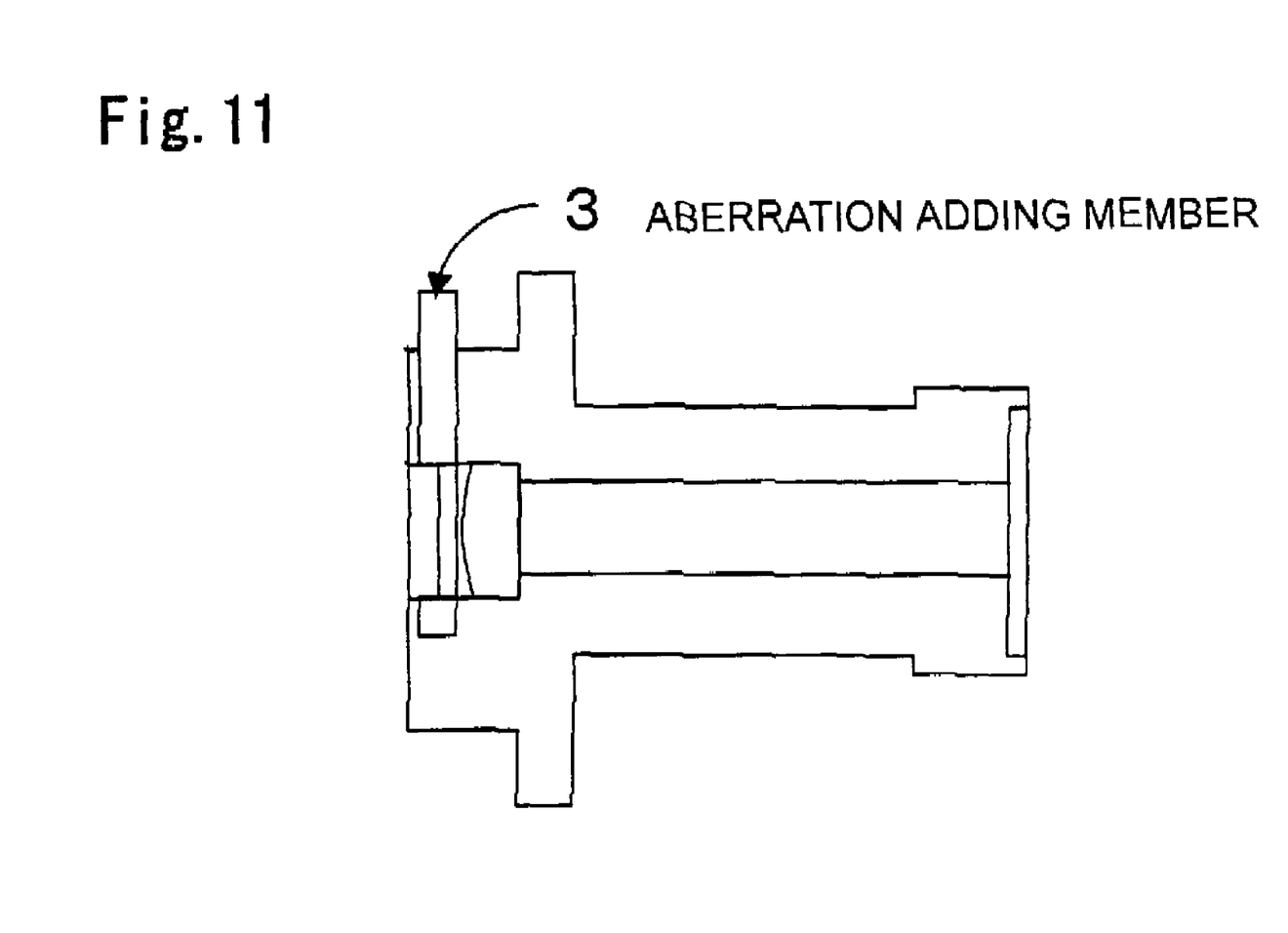
FIG. 11 is a view showing the construction of a fourth embodiment of the model eye for an eye characteristic measuring device according to the invention.

FIG. 11 is a view showing the construction of a fourth embodiment of the model eye for an eye characteristic measuring device. In the fourth embodiment, the aberration adding member 3 is disposed before the anterior eye lens 1.

Design and manufacture examples of the model eye will be described below.

(1) Model eyes are manufactured for individual degrees of refractive power and individual degrees of astigmatic power. For example, if model eyes are designed so that the distance from the front surface of the anterior eye lens 1 (that corresponds to the front surface of the cornea) to the fundus is kept constant for all the model eyes, metal parts of the same shape can be used for the model eyes.

(2) A model eye is manufactured which is free from aberrations at a certain degree of refractive power and makes it possible to measure aberrations at various degrees of refractive power by modifying the position of the fundus. Since an aberration (longitudinal aberration) occurs when the position of the fundus is modified, the design of the phase plate 31 needs to taken such aberration into account. In this case, the anterior eye lens 1 can use, for example, a cemented lens.

(3) A model eye may also be manufactured by using a lens which can be kept free from aberrations even if the position of the fundus is moved to a certain extent. In this case, the anterior eye lens 1 is designed as an arrangement of lens groups.

Prerequisite (necessary) conditions for the design of the model eye will be described below by way of example.

(1) The amount of aberration to be added is given on the basis of the supposed predetermined incident diameter of the phase plate 31 that corresponds to a pupil diameter to be analyzed.

(2) The modification of the amount of aberration is performed by replacing the aberration adding member 3 with another aberration adding member which is given a phase amount for a different amount of aberration.

(3) The modification of conditions relative to myopia astigmatism, hyperopia and the like is performed by disposing the diffusion surface 2 at an image point position relative to an object point position corresponding to a power (refractive power) given to the model eye or by replacing the anterior eye lens 1 with a lens corresponding to astigmatic components and a power (refractive power) given to the model eye.

Power and aberration to be given to the model eye can be formed by two kinds of methods as will be described below by way of example.

(1) The anterior eye lens 1 having no aberrations is prepared, and a desired power and aberration are given to the anterior eye lens 1 in such a way that the power is determined depending on only the lens 1 and the aberration is determined depending on only the phase plate 31.

(2) In the case where the anterior eye lens 1 has a residual power aberration, the phase plate 31 is given an aberration to take the residual power aberration into account, or the phase plate 31 is given an aberration without taking the residual power aberration into account. Then, a phase amount to be given to the phase plate 31 is determined to take into account a designed aberration value or a measured aberration of the anterior eye lens 1, or measured eye characteristic data are examined by taking into account a designed aberration value or a measured aberration of the anterior eye lens 1. Incidentally, the residual power aberration of the anterior eye lens 1 is found by, for example, a method using ray tracing or a method using general formulas.

Aberration will be described below.

Figure 6:
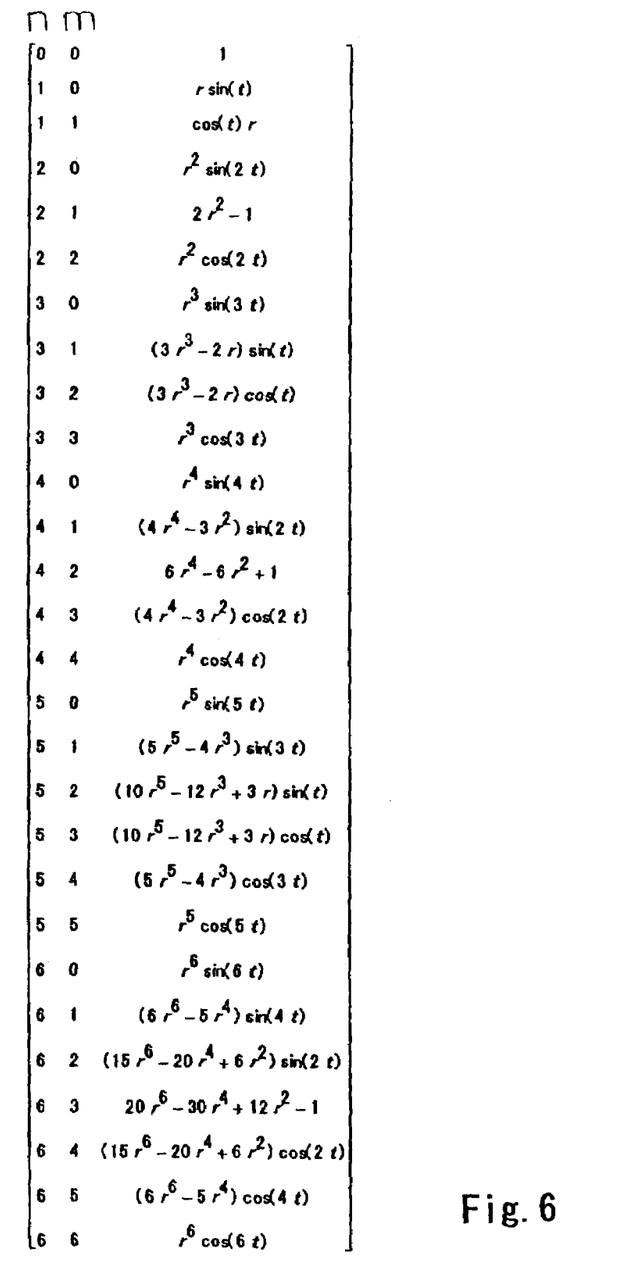
FIG. 6 is a view (1) showing the values of a Zernike polynomial.

In association with an aberration W(r) to be given to the model eye (an aberration to be given as a measured value), the diameter of a light beam to be given to the phase plate 31 is determined from the relationship between the diameter of a light beam exiting from the model eye and the diameter of a light beam passing through the phase plate 31. An aberration to be given to the phase plate 31 is assumed to correspond to each term of a Zernike circle polynomial such as the following equation:

$$W(r) = A\lambda \cdot Z_n^m(r),$$

where r is the diameter of a light beam to be made incident on the phase plate 31 with respect to a pupil diameter $r_{pupil}$ to be measured, A is a constant ($\lambda$) indicative of the magnitude of an aberration amount, $\lambda$ is a designed wavelength, and $Z_n^m(r)$ is a Zernike polynomial. FIG. 6 is a view (1) showing the values of the Zernike polynomial.

Figure 7:
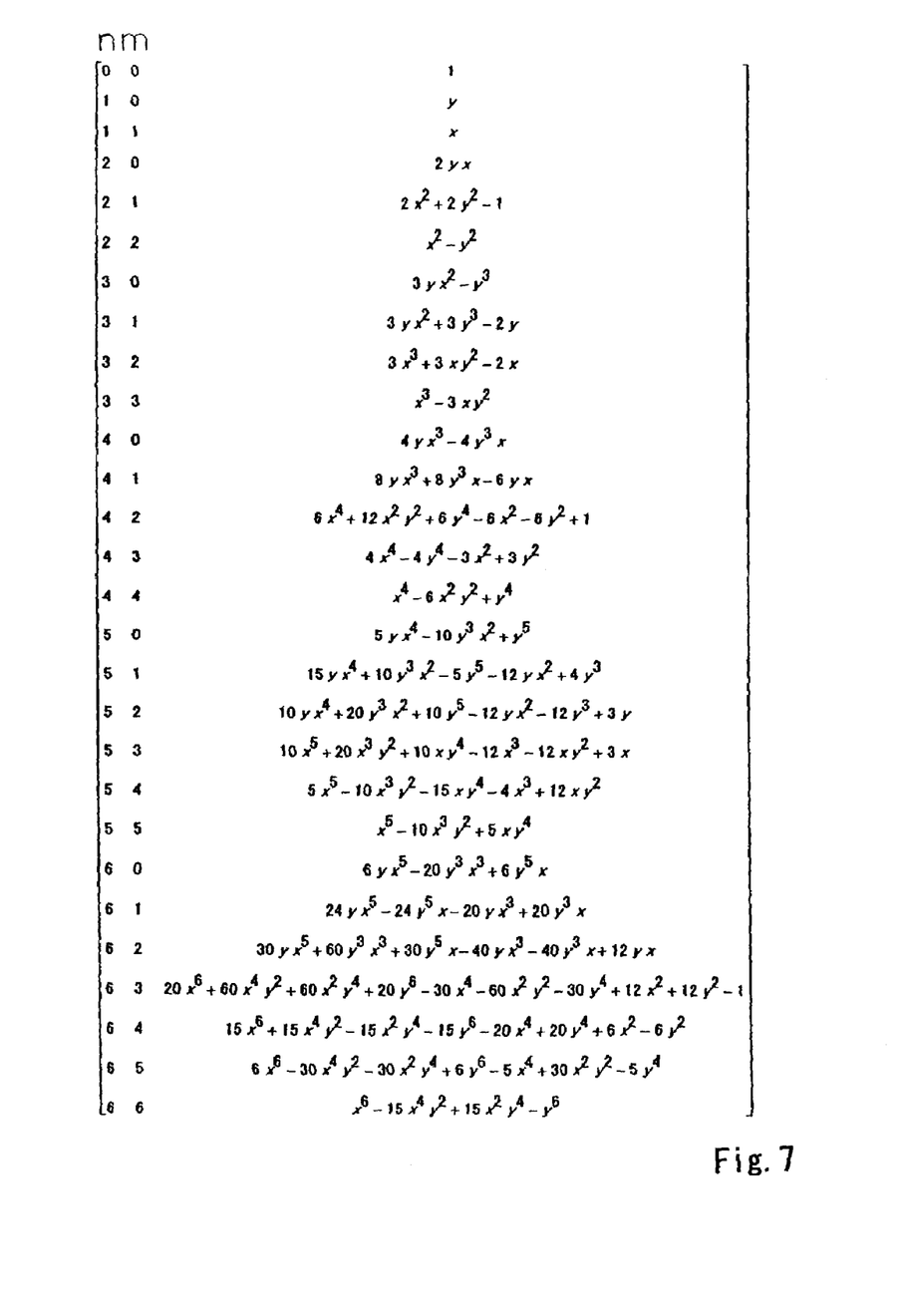
FIG. 7 is a view (2) showing the values of the Zernike polynomial.

Incidentally, the r coordinate may be converted to x, y coordinates. FIG. 7 is a view (2) showing the values of the Zernike circle polynomial for this case.

2. Calibration Method for Model Eye for Eye Characteristic Measuring Device

A method of confirming the aberration of the entire model eye including the anterior eye lens 1 and the aberration adding member 3 (the phase plate 31), by using an interferometer will be described below.

Figure 8:
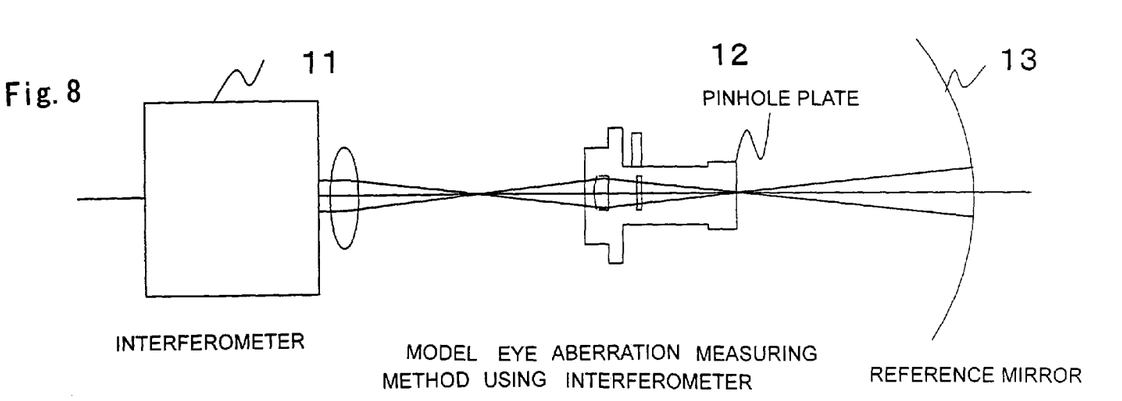
FIG. 8 is a view showing the construction of a calibration device for the model eye for an eye characteristic measuring device.

FIG. 8 is a view showing the construction of a calibration device for the model eye for an eye characteristic measuring device. The shown calibration device includes an interferometer 11, a pinhole plate 12 and a reference mirror 13. In each of the above-described embodiments, the diffusion surface 2 is constructed to be removably attached to the model eye, and the pinhole plate 12 having a pinhole formed in a fundus portion is attached to the model eye in place of the diffusion surface 2 and is subjected to alignment, and the optical characteristics (optical aberrations) of the model eye are measured with the interferometer 11. The optical characteristics of the model eye are estimated from the measured result, and the pinhole plate 12 is replaced with the diffusion surface 2, thus preparing the model eye.

2-1. Preparation for Measurement

The positional relationship between the interferometer 11 and the model eye is adjusted so that light converges at the pinhole position of the pinhole plate 12 disposed in place of the diffusion surface 2 with respect to the anterior eye lens 1 and the aberration adding member 3 of the model eye. The pinhole of the model eye is disposed to approximately coincide with the center of curvature of the reference mirror 13.

2-2. Measurement Procedure

In the case where the interferometer 11, the pinhole plate 12 and the reference mirror 13 are arranged in accordance with the above-described preparation for measurement, a light beam emitted from the interferometer 11 converges at a position conjugated with the pinhole with respect to the anterior eye lens 1 and the phase plate 31, and the light beam again converges at the position of the pinhole so that the light beam passes through the pinhole. Then, the light beam which has passed through the pinhole is reflected by the reference mirror 13, and again passes through the pinhole and returns to the interferometer 11 as a measurement light beam. Although not shown, the interferometer 11 causes the measurement light beam and the reference light beam reflected from the reference mirror 13 to interfere with each other by means of a beam splitter or the like, and measures the aberration amount and the optical characteristics of the entire model eye from the obtained interference fringes.

3. Manufacture and Design of Plural Kinds of Model Eyes

Means for manufacturing and designing various model eyes having different degrees of refractive power, different degrees of astigmatic power and different aberrations will be described below.

A model eye can be constructed so that at least one characteristic element selected from among the refractive power, the astigmatism and the astigmatism axis of the model eye can be modified, by means of any one of constructions which will be described below by way of example or by means of a combination of any ones of the constructions.

(1) Constructions for Formation and Modification of Various Degrees of Refractive Power A construction in which the position of the diffusion surface 2 is movable in the direction of the optical axis at least.

A construction in which the power of the anterior eye lens 1 is modifiable; for example, the anterior eye lens 1 is made of a zoom lens system so that the focal length of the anterior eye lens 1 can be modified, and some lenses of the zoom lens system are moved in the direction of the optical axis to modify the entire focal length, thereby modifying the power of the anterior eye lens 1.

A construction in which the anterior eye lens 1 is movable in the direction of the optical axis.

(2) Constructions for Formation, Addition and Modification of Various Degrees of Astigmatic Power A construction in which a cylindrical lens component such as a cylindrical lens can be added and modified.

A construction in which a variable cross-cylinder is inserted so that the angle of rotation thereof can be changed to modify the cross angle of the cylindrical lens.

(3) Construction for Formation, Addition and Modification of Various Aberrations A construction in which the aberration adding member 3 is modifiable.

The anterior eye lens 1 is preferably formed of a lens such as a combination of a plurality of lens elements and/or a cemented lens so that the model eye is designed so that even if conditions are modified, variations in the influence of aberration due to the anterior eye lens 1 become as small as possible. In this case, it is possible to adopt, for example, a lens of a symmetrical type such as a Gaussian type, an aspherical lens, a group of lenses using glasses having a rich variety of refractive indices, or a triplet.

Furthermore, there is a case of determining the power of the model eye by moving only the fundus position, and there is also a method of forming a zoom lens by combining a plurality of lenses. Furthermore, there is a case of replacing the aberration adding member 3 according to variations in conditions.

Design and manufacture examples of model eyes having various degrees of refractive power, various degrees of astigmatic power or various aberrations will be described below.

Figure 9:
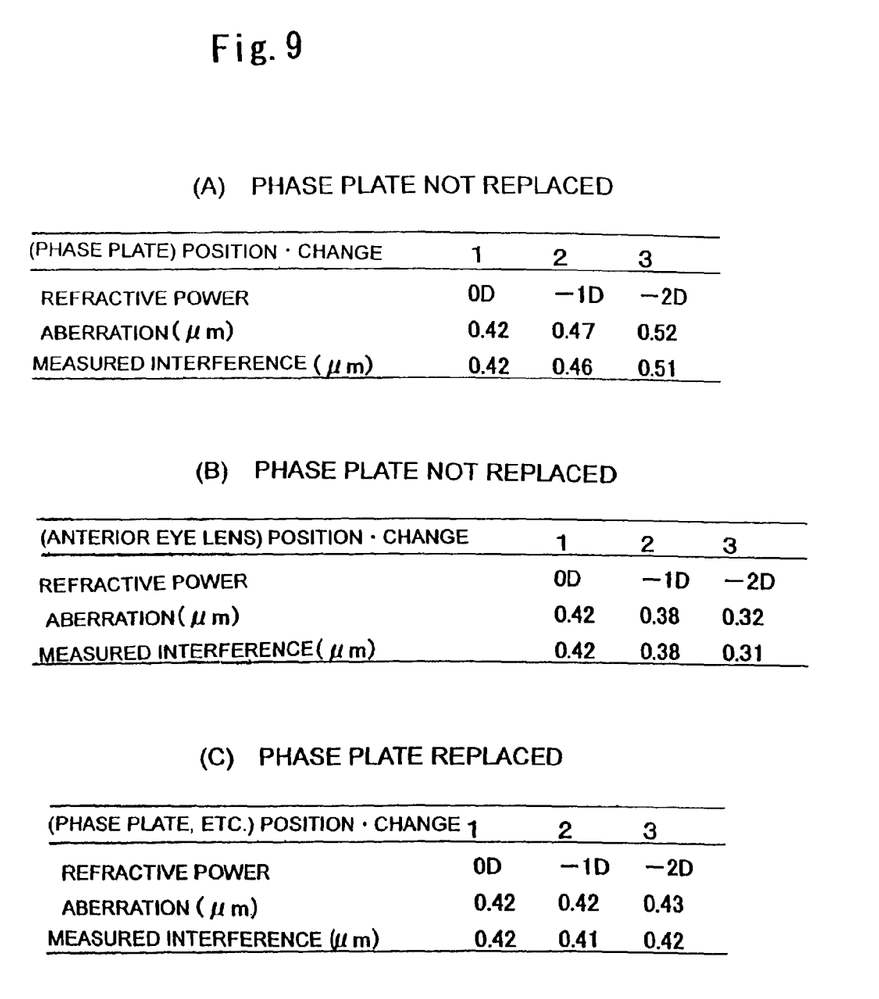

FIGS. 9A to 9C are explanatory views of design and manufacture examples of various model eyes.

The shown examples are examples of $W(r)=A\lambda \cdot Z_n^m(r)$ with $A=0.5$ and $\lambda=840$ nm. FIG. 9A shows the case where only the diffusion surface 2 is moved without the replacement of the aberration adding member 3 (the phase plate 31). FIG. 9B shows the case where only the anterior eye lens 1 is moved without the replacement of the aberration adding member 3 (the phase plate 31). FIG. 9C shows the case where the aberration adding member 3 (the phase plate 31) is replaced or moved and only the diffusion surface 2 is moved. Incidentally, it is also possible to adopt a construction in which the aberration adding member 3 (the phase plate 31) is replaced or moved and only the anterior eye lens 1 is moved. Furthermore, it is possible to adopt a construction in which the aberration adding member 3 (the phase plate 31) is not replaced or moved and both the anterior eye lens 1 and the diffusion surface 2 are moved, or in which the aberration adding member 3 (the phase plate 31) is replaced or moved and both the anterior eye lens 1 and the diffusion surface 2 are also moved.

4. Measurement of Corneal Aberration

Figure 10:
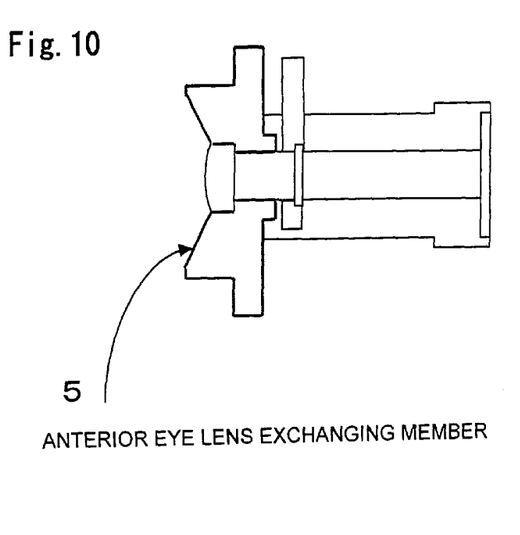
FIG. 10 is a view showing the construction of a fifth embodiment of the model eye for an eye characteristic measuring device according to the invention.

FIG. 10 is a view showing the construction of a fifth embodiment of the model eye for an eye characteristic measuring device. In the fifth embodiment, it is possible to measure the corneal shape of the front surface of the anterior eye lens 1 that corresponds to the cornea. The front surface of the anterior eye lens 1 is made of, for example, a spherical surface, an aspherical surface and a toric surface, and the radius of curvature of the front surface can be made to approximate a general radius of curvature of the front surface of the cornea (for example, 7.5 mm). An anterior eye lens exchanging member 5 of the type shown in FIG. 10 can be replaced with another anterior eye lens exchanging member having the anterior eye lens 1 whose front surface has a different radius of curvature or surface shape, whereby the fifth embodiment makes it possible to measure various corneal shapes. In the fifth embodiment, in the case where the shape of the front surface of the anterior eye lens exchanging member 5 is made conical, it is possible to measure the shape of the cornea with a light beam having an angle, whereby it is possible to realize more accurate measurement. In addition, in the case of an eye characteristic measuring device capable of measuring at the same time the corneal shape of an eye and the aberrations of the entire eye, the model eye of the fifth embodiment can be used to perform calibrating measurement at the same time. In addition, the anterior eye lens exchanging member 5 alone can also be used as a model eye for calibrating only the corneal shape.

In each of the above-described embodiments, the diffusion surface 2 can also be constructed to be finely vibrated in directions perpendicular to the optical axis or to rotate about an axis parallel to the optical axis. This construction has the advantage that nonuniform reflection at the diffusion surface 2 can be eliminated.

What is claimed is:

1. A model eye for an eye characteristic measuring device, comprising:
    an anterior eye lens forming a predetermined power to be given to the model eye;
    a diffusion surface diffusing and reflecting incident light, the diffusion surface being disposed at an image point position corresponding to the predetermined power in relationship to the anterior eye lens; and
    a phase plate giving a predetermined aberration to an area between the anterior eye lens and the diffusion surface, wherein power and aberration required for the model eye are formed by the anterior eye lens and the phase plate,
    wherein the phase plate is disposed to be tilted at a predetermined angle with respect to an optical axis to eliminate an influence of reflection, a binary optics element (BOE) which forms the phase plate being formed to take the tilt of the phase plate into account.

2. A model eye for an eye characteristic measuring device, comprising:
    an anterior eye lens forming a predetermined power to be given to the model eye;
    a diffusion surface diffusing and reflecting incident light, the diffusion surface being disposed at an image point position corresponding to the predetermined power in relationship to the anterior eye lens; and
    a phase plate giving a predetermined aberration to an area between the anterior eye lens and the diffusion surface, wherein power and aberration required for the model eye are formed by the anterior eye lens and the phase plate,
    wherein the anterior eye lens is formed of a lens having a residual aberration, the phase plate being constructed to cancel the residual aberration and give the predetermined aberration.

3. A model eye for an eye characteristic measuring device, comprising:
    an anterior eye lens forming a predetermined power to be given to the model eye;
    a diffusion surface diffusing and reflecting incident light, the diffusion surface being disposed at an image point position corresponding to the predetermined power in relationship to the anterior eye lens; and
    a phase plate giving a predetermined aberration to an area between the anterior eye lens and the diffusion surface, wherein power and aberration required for the model eye are formed by the anterior eye lens and the phase plate,
    wherein the model eye is constructed to have astigmatic power or cylindrical power capable of being added and/or changed by at least one of a construction in which a cylindrical lens can be added and/or changed and a construction which is provided with a variable cross-cylinder to make the cylindrical lens modifiable in cross angle.

4. A model eye for an eye characteristic measuring device, comprising:
    an anterior eye lens forming a predetermined power to be given to the model eye;
    a diffusion surface diffusing and reflecting incident light, the diffusion surface being disposed at an image point position corresponding to the predetermined power in relationship to the anterior eye lens; and
    a phase plate giving a predetermined aberration to an area between the anterior eye lens and the diffusion surface, wherein power and aberration required for the model eye are formed by the anterior eye lens and the phase plate,
    wherein at least the phase plate is constructed to be changeable so that the model eye is changeable in aberration.

5. A model eye for an eye characteristic measuring device intended for emmetropia as in claim 1, 2, 3, or 4, wherein the diffusion surface is disposed approximately at a focal length position of the anterior eye lens.

6. A model eye for an eye characteristic measuring device as in claim 1, 2, 3, or 4, wherein the diffusion surface has a reflectance of 10% or less.

7. A model eye for an eye characteristic measuring device as in claim 1, 2, 3, or 4, wherein the anterior eye lens includes a lens having as small aberrations as possible, the anterior eye lens being designed so that variations in an influence of aberration due to the anterior eye lens become as small as possible even if conditions are modified.

8. A model eye for an eye characteristic measuring device as in claim 1, 2, 3, or 4, further comprising a housing covering the anterior eye lens, the phase plate and the diffusion surface, the housing being constructed to prevent foreign material from adhering to the diffusion surface and the phase plate.

9. A model eye for an eye characteristic measuring device as in claim 1, 2, 3, or 4, wherein the diffusion surface is disposed approximately at an image plane position in an object-image relationship corresponding to the power to be given to the model eye.

10. A model eye for an eye characteristic measuring device as in claim 1, 2, 3, or 4, wherein the model eye is constructed to be changeable in its refractive power by at least one construction selected from a construction in which the diffusion surface is movable in the direction of the optical axis, a construction in which the anterior eye lens includes a zoom lens system so that the anterior eye lens is modifiable in focal length, and a construction in which the anterior lens is movable in the direction of the optical axis.

11. A calibration method for a model eye for an eye characteristic measuring device, the model eye comprising an anterior eye lens forming a predetermined power to be given to the model eye, a diffusion surface diffusing and reflecting incident light, the diffusion surface being disposed at an image point position corresponding to the predetermined power in relationship to the anterior eye lens, and a phase plate giving a predetermined aberration to an area between the anterior eye lens and the diffusion surface, power and aberration required for the model eye being formed by the anterior eye lens and the phase plate, the calibration method comprising:

attaching a pinhole plate in place of the diffusion surface which is removably constructed;

performing alignment;

measuring optical characteristics with an interferometer;

estimating the optical characteristics of the model eye from the measured result; and replacing the pinhole plate with the diffusion surface to calibrate the model eye, wherein the model eye is constructed to have astigmatic power or cylindrical power capable of being added and/or changed by at least one of a construction in which a cylindrical lens can be added and/or changed and a construction which is provided with a variable cross-cylinder to make the cylindrical lens modifiable in cross angle.

12. A calibration method for a model eye for an eye characteristic measuring device, the model eye comprising an anterior eye lens forming a predetermined power to be given to the model eye, a diffusion surface diffusing and reflecting incident light, the diffusion surface being disposed at an image point position corresponding to the predetermined power in relationship to the anterior eye lens, and a phase plate giving a predetermined aberration to an area between the anterior eye lens and the diffusion surface, power and aberration required for the model eye being formed by the anterior eye lens and the phase plate, the calibration method comprising:

attaching a pinhole plate in place of the diffusion surface which is removably constructed;

performing alignment;

measuring optical characteristics with an interferometer;

estimating the optical characteristics of the model eye from the measured result; and replacing the pinhole plate with the diffusion surface to calibrate the model eye, wherein at least the phase plate is constructed to be changeable so that the model eye is changeable in aberration.

13. A calibration method for a model eye for an eye characteristic measuring device intended for emmetropia as in claim 11 or 12, wherein the diffusion surface is disposed approximately at a focal length position of the anterior eye lens.

14. A calibration method for a model eye for an eye characteristic measuring device as in claim 11 or 12, wherein the diffusion surface is disposed approximately at an image plane position in an object-image relationship corresponding to the power to be given to the model eye.

15. A calibration method for a model eye for an eye characteristic measuring device as in claim 11 or 12, wherein the anterior eye lens includes a front surface having a radius of curvature approximately equal to a radius of curvature of a cornea and is removably constructed to enable an anterior eye lens having a front surface of different radius of curvature to be fitted to the model eye, wherein calibration for corneal-shape measurement of an eye characteristic measuring device having a corneal shape measuring function can be made under various states in each of which an anterior eye lens having a front surface of different radius of curvature is fitted to the model eye.

* * * * *

UNITED STATES PATENT AND TRADEMARK OFFICE
CERTIFICATE OF CORRECTION

| | |
|---|---|
| PATENT NO. | : 7,036,933 B2 |
| APPLICATION NO. | : 10/365618 |
| DATED | : May 2, 2006 |
| INVENTOR(S) | : Yamaguchi et al. |

Page 1 of 1

It is certified that error appears in the above-identified patent and that said Letters Patent is hereby corrected as shown below:

On the title page item (*) Notice line 3, "485" shold read -- 456 --.

Signed and Sealed this

Third Day of July, 2007

JON W. DUDAS
*Director of the United States Patent and Trademark Office*